United States Patent [19]

Nishikawa

[11] Patent Number: 5,736,561
[45] Date of Patent: *Apr. 7, 1998

[54] VASCULAR HYPERTROPHY SUPPRESSOR

[75] Inventor: Kohei Nishikawa, Kyoto, Japan

[73] Assignee: Takeda Chemical Industries, Ltd., Osaka, Japan

[*] Notice: The term of this patent shall not extend beyond the expiration date of Pat. No. 5,508,297.

[21] Appl. No.: 588,240

[22] Filed: Jan. 18, 1996

Related U.S. Application Data

[62] Division of Ser. No. 201,122, Feb. 24, 1994, Pat. No. 5,508,297.

[30] Foreign Application Priority Data

Feb. 25, 1993 [JP] Japan ................. 5-036630

[51] Int. Cl.$^6$ .......... A61K 31/41; C07D 271/06
[52] U.S. Cl. .......... 514/364; 514/361; 514/381; 548/129; 548/132; 548/253; 548/254
[58] Field of Search .......... 548/129, 132, 548/250, 251, 252, 253, 254; 514/363, 364, 381

[56] References Cited

U.S. PATENT DOCUMENTS

| | | | |
|---|---|---|---|
| 5,128,356 | 7/1992 | Naka et al. | 514/381 |
| 5,162,326 | 11/1992 | Naka et al. | 514/269 |
| 5,166,143 | 11/1992 | Ondetti et al. | 514/89 |
| 5,183,899 | 2/1993 | Naka et al. | 548/253 |
| 5,210,211 | 5/1993 | Hodges et al. | 548/314.7 |
| 5,243,054 | 9/1993 | Naka et al. | 548/132 |
| 5,250,554 | 10/1993 | Naka et al. | 514/381 |
| 5,284,661 | 2/1994 | Morimoto et al. | 424/464 |
| 5,328,919 | 7/1994 | Naka et al. | 514/381 |

FOREIGN PATENT DOCUMENTS

| | | |
|---|---|---|
| 400835 | 12/1990 | European Pat. Off. |
| 0 425 921 | 5/1991 | European Pat. Off. |
| 0 430 300 | 6/1991 | European Pat. Off. |
| 0 434 038 | 6/1991 | European Pat. Off. |
| 0 445 811 | 9/1991 | European Pat. Off. |
| 0 459 136 | 12/1991 | European Pat. Off. |
| 0 461 039 | 12/1991 | European Pat. Off. |
| 0 483 683 | 5/1992 | European Pat. Off. |
| 0 518 033 | 12/1992 | European Pat. Off. |
| 0 520 423 | 12/1992 | European Pat. Off. |
| 0 552 765 | 7/1993 | European Pat. Off. |
| 0 588 299 | 3/1994 | European Pat. Off. |
| 0 603 712 | 6/1994 | European Pat. Off. |
| 92/10185 | 6/1992 | WIPO. |

OTHER PUBLICATIONS

Linz et al., Molecular and Cellular Biochemistry, vol. 147, pp. 89–97, 1995.

Stedman's Medical Dictionary, 25th Edition, pp. 744, 746, and 747, 1991.

Kawamura et al., "TCV–116, A Novel Angiotensin II Receptor Antagonist, Prevents Intimal Thickening And Impairment of Vascular Function After Carotid Injury in Rats", *The Journal of Pharmacology and Experimental Therapeutics*, vol. 266, No. 3, pp. 1664–1669, (1993).

Yokohama, *The Japanese Journal of Pharmacology*, vol. 61, pp. 115P, (1993).

Azuma et al., "Prevention of Intimal Thickening After Endothelial Removal by a Nonpeptide Angiotensin II Receptor Antagonist, Losartan", *british journal of Pharmacology*, vol. 106, No. 3, pp. 665–671, (1992).

Prescott et al., "Angiotensin–Converting Enzyme Inhibitor Versus Angiotensin II, AT, Receptor Antagonist", *The American Journal of Pathology*, vol. 139, No. 6, pp. 1291–1296, (1991).

Osterrieder et al., "Role of Angiotensin II in Injury–Induced Neointima Formation in Rats", *Hypertension*, vol. 18, no. S1, pp. II-60–II-64, (1991).

Mizuno et al., "Hypotensive Activity of TCV–116, A Newly Developed angiotensin II Receptor Antagonist, In Spontaneously Hypertensive Rates", *Life Sciences*, vol. 51, pp. PL 183–187, (1992).

*Primary Examiner*—Joseph McKane
*Attorney, Agent, or Firm*—Foley & Lardner

[57] ABSTRACT

This invention relates to a method for the prophylaxis or treatment of vascular hypertropy in a mammal by administering a pharmaceutically effective amount of a compound represented by the formula (I):

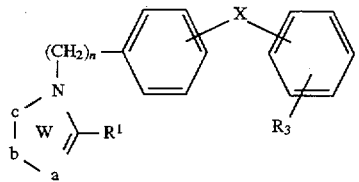

wherein ring W is a nitrogen-containing heterocyclic ring residue which may be substituted; $R^1$ is hydrogen or an optionally substituted hydrocarbon residue which optionally binds through a hetero-atom; $R^3$ represents a group capable of forming an anion or a group capable of changing thereto; X shows that the phenylene and phenyl groups bind to each other directly or through a spacer having an atomic length of two or less; n denotes 1 or 2; a and b forming the heterocyclic ring residue are independently one or two optionally substituted carbon or hetero atoms; c is an optionally substituted carbon or hetero atom; provided that, when the ring W is a condensed ring, $R^1$ is hydrogen or an optionally substituted hydrocarbon residue which binds through a hetero atom, or a salt thereof to a mammal in need thereof.

21 Claims, No Drawings

VASCULAR HYPERTROPHY SUPPRESSOR

This application is a division of application Ser. No. 08/201,122, filed Feb. 24, 1994, now U.S. Pat. No. 5,508,297.

FIELD OF THE INVENTION

This invention relates to a vascular hypertrophy suppressor comprising a compound (or salt thereof) exhibiting angiotensin II antagonistic action and having excellent vascular hypertrophy inhibitory actions as an active ingredient.

BACKGROUND OF THE INVENTION

Easy and safe angiography has become feasible as a result of technical advances, development and improvement of radiographs and development of safe contrast media. Angiographic methods are roughly divided into two types: arterial angiography and venous angiography, including (1) methods in which the artery or vein is directly perforated percutaneously (carotid arteriography, vertebral arteriography, femoral arteriography, brachial arteriography, pelvic venography, lower limb venography), (2) methods in which the artery or vein is surgically exposed, incised and catheterized for imaging (cardiovascular angiography, inferior vena cava venography, pulmonary arteriography), (3) methods in which a catheter is inserted percutaneously by the Seldinger technique (peritoneal arteriography, abdominal aortic arteriography, renal arteriography, inferior vena cava venography, hepatic venography) and (4) methods in which a contrast medium is injected to the vein or artery and the arterial or venous phase is photographed. The development of the Seldinger technique made possible percutaneous intravascular catheterization (intravascular catheterization requires a surgical procedure in prior art methods), leading to remarkable advances in angiography.

Objectives of angiography include 1) qualitative and quantitative evaluation of lesions in blood vessels, 2) qualitative and quantitative evaluation of lesions in various organs and surrounding tissues on the basis of vascular exclusion and/or invasion pictures, 3) dynamic and functional evaluation of blood vessels by continuous imaging of contrast medium flow, and 4) anticancer agent injection to lesions via blood vessels. Advances in imaging techniques have markedly improved bypass (shunt) surgical treatment. Bypass surgery, a type of blood route reconstructive surgery for obstructed blood vessels, constructs a bypass from the proximal to distal sides of the obstructed portion (bypass transplantation), including aortocoronary bypass, aortoiliac bypass and cardiopulmonary bypass.

However, vascular perforation in angiography and vascular cutting, suturing etc. in bypass surgery can cause vascular hypertrophy, since they affect the blood vessel by direct physical stimulation.

Compounds exhibiting angiotensin II antagonistic action, used in the present invention, are known to serve as therapeutic agents for circulatory diseases such as hypertension, heart diseases (heart hypertrophy, heart failure, myocardial infarction etc.), cerebral stroke and nephritis (e.g., Japanese Patent Unexamined Publication No. 364171/1992). Concerning their mechanism of action, inhibition of the binding to angiotensin II receptors of angiotensin II, a potent vasoconstrictor, has been suggested.

OBJECT OF THE INVENTION

The present invention is to provide a vascular hypertrophy suppressor, such as a pharmaceutical preparation which serves well to suppress and prevent or treat vascular hypertrophy (including restenosis) after percutaneous transluminal coronary angioplasty (PTCA), vascular restenosis after bypass surgery and progress of arteriosclerosis.

SUMMARY OF THE INVENTION

Against this background the present inventors, in investigating drugs which suppress vascular hypertrophy (including restenosis), stumbled upon the fact that angiotensin II antagonizing compounds are effective in suppressing and preventing or treating vascular hypertrophy (including restenosis) after percutaneous transluminal coronary angioplasty (PTCA), vascular restenosis after bypass surgery and progress of arteriosclerosis. The inventors made further investigations based on this finding, and developed the present invention.

Accordingly, the present invention relates to a vascular hypertrophy suppressor comprising as an active ingredient a compound represented by the formula (I):

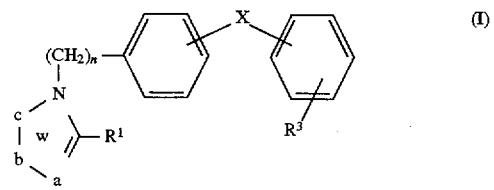

wherein ring W is a nitrogen-containing heterocyclic residue which may be substituted; $R^1$ is hydrogen or an optionally substituted hydrocarbon residue which optionally binds through a hetero-atom; $R^3$ represents a group capable of forming an anion or a group capable of changing thereto; X shows that the phenylene and phenyl groups bind to each other directly or through a spacer having an atomic length of two or less; n denotes 1 or 2; a and b forming the heterocyclic ring residue are independently one or two optionally substituted carbon or hetero atoms; c is an optionally substituted carbon or hetero atom; provided that, when the ring W is a condensed ring, $R^1$ is hydrogen or an optionally substituted hydrocarbon residue which binds through a hetero atom, or a salt thereof.

DETAILED DESCRIPTION OF THE INVENTION

The angiotensin II antagonizing compound of the present invention, represented by general formula (I), can be advantageously used to suppress and prevent or treat vascular hypertrophy resulting from direct physical stimulation of the blood vessel by vascular perforation in angiography, vascular cutting, suturing etc. in bypass surgery. For example, it is used to suppress and prevent or treat vascular hypertrophy (including restenosis) after percutaneous transluminal coronary angioplasty (PTCA) and vascular restenosis after bypass surgery. It can also be advantageously used to suppress and prevent or treat vascular hypertrophy due to arteriosclerosis.

Examples of the hydrocarbon residue represented by $R^1$ include alkyl, alkenyl, alkynyl, cycloalkyl, aryl and aralkyl groups. Among them alkyl, alkenyl and cycloalkyl groups are preferable. The hydrocarbon residue may bind to the ring W through a hetero atom.

The alkyl group represented by $R^1$ is a straight-chain or branched lower alkyl group having 1 to about 8 carbon atoms, as exemplified by methyl, ethyl, propyl isopropyl, butyl, isobutyl, sec-butyl, t-butyl, pentyl, i-pentyl, hexyl, heptyl or octyl.

The alkenyl group represented by $R^1$ is a straight-chain or branched lower alkenyl group having 2 to about 8 carbon atoms, as exemplified by vinyl, propenyl, 2-butenyl, 3-butenyl, isobutenyl or 2-octenyl.

The alkynyl group represented by $R^1$ is a straight-chain or branched lower alkynyl group having 2 to about 8 carbon atoms, as exemplified by ethynyl, 2-propinyl, 2-butynyl, 2-pentynyl or 2-octynyl.

The cycloalkyl group represented by $R^1$ is a lower cycloalkyl group having 3 to about 6 carbon atoms, as exemplified by cyclopropyl, cyclobutyl, cyclopentyl or cyclohexyl.

The above-mentioned alkyl, alkenyl, alkynyl or cycloalkyl group may optionally be substituted with hydroxyl group, an optionally substituted amino group (e.g. amino, N-lower ($C_{1-4}$) alkylamino or N,N-dilower ($C_{1-4}$) alkylamino), halogen, a lower ($C_{1-4}$) alkoxy group, a lower ($C_{1-4}$) alkylthio group.

The aralkyl group represented by $R^1$ is, for example, a phenyl-lower ($C_{1-4}$) alkyl such as benzyl or phenethyl, and the aryl group represented by $R^1$ is, for example, phenyl.

The above-mentioned aralkyl or aryl group may optionally have, on any position of its benzene ring, for example, halogen (e.g. F, Cl or Br), nitro, an optionally substituted amino group (e.g. amino, N-lower ($C_{1-4}$) alkylamino or N,N-dilower ($C_{1-4}$) alkylamino), lower ($C_{1-4}$) alkoxy (e.g. methoxy or ethoxy), lower ($C_{1-4}$) alkylthio (e.g. methylthio or ethylthio) or lower ($C_{1-4}$) alkyl (e.g. methyl or ethyl).

Among the above-mentioned groups represented by $R^1$, optionally substituted alkyl, alkenyl or cycloalkyl groups (e.g. a lower ($C_{1-5}$) alkyl, lower ($C_{2-5}$) alkenyl or lower ($C_{3-6}$) cycloalkyl group optionally substituted with hydroxyl group, amino group, halogen or a lower ($C_{1-4}$) alkoxy group) are preferable.

The above-mentioned $R^1$ may optionally bind through a hereto-atom (e.g. nitrogen ($N(R^9)$) ($R^9$ stands for hydrogen or a lower ($C_{1-4}$) alkyl)), oxygen or sulfur ($—S(O)_m—$ (m denotes an integer of 0 to 2)), etc.), and, among them, optionally substituted alkyl or alkenyl group bound through a hereto-atom (e.g. methylamino, ethylamino, propylamino, propenylamino, isopropylamino, allylamino, butylamino, isobutylamino, dimethylamino, methylethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, sec-butylthio, t-butylthio, 2-butenylthio, 3-butenylthio, isobutenylthio, pentylthio, isopentylthio, hexylthio, etc.) are preferable.

With respect to formula (I) above, the group for $R^3$, capable of forming an anion (a group having a hydrogen atom capable of leaving as a proton), or a group capable of changing thereto, is exemplified by 5- to 7-membered (preferably 5- or 6-membered) monocyclic heterocyclic ring residues which contain one or more of N, S and O and which may be substituted (preferably N-containing heterocyclic residue having hydrogen atom capable of leaving as a proton), and groups capable of changing thereto in vivo. Such groups include the following:

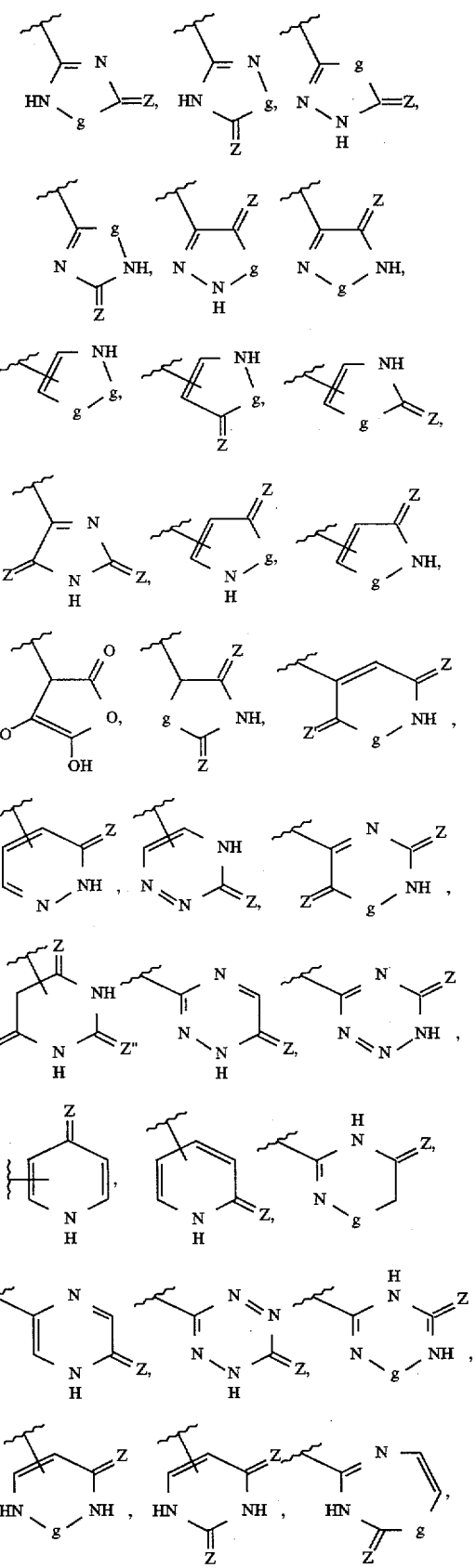

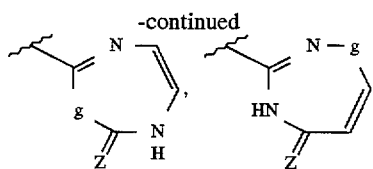

The chemical bond between the group for R³ and the partner phenyl group may be a carbon-carbon bond as shown above, or a nitrogen-carbon bond via one of the several nitrogen atoms when the symbol g represents —NH— in the above formulas.

For example, when R³ stands for a group

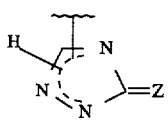

it stands for

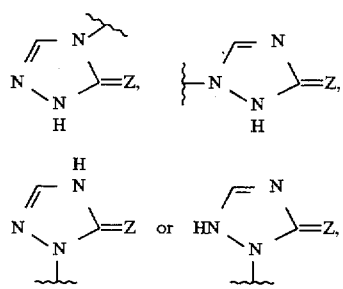

Other examples of R³ binding through nitrogen atom include

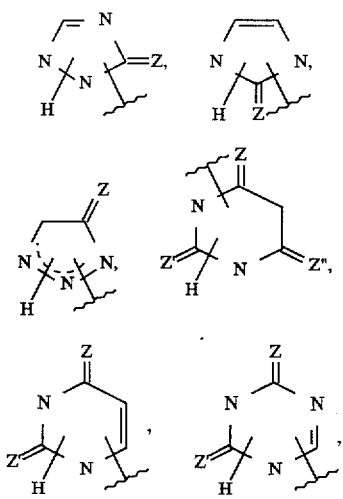

[In the above formula, g stands for —CH₂—, —NR⁹—, O atom or

>=Z, >=Z' and >=Z" respectively stand for carbonyl group, thiocarbonyl group or an optionally oxidized sulfur atom (e.g. S, S(O), S(O)₂, etc.), preferably carbonyl or thiocarbonyl group, more preferably carbonyl; m denotes 0, 1 or 2; and R⁹ stands for hydrogen atom or an optionally substituted lower alkyl group].

Preferable examples of R³ include 2,5-dihydro-5-oxo-1, 2,4-oxadiazole ring residue, 2,5-dihydro-5-thioxo-1,2,4-oxadiazole ring residue or 2,5-dihydro-5-oxo-1,2,4-thiadiazole ring residue having —NH or —OH group as proton donor and carbonyl group, thiocarbonyl group or sulfinyl group as proton acceptor simultaneously.

And, while the heterocyclic residue represented by R³ may form a condensed ring by connecting the substituents on the ring, it is preferably a 5- to 6-membered ring, more preferably a 5-membered heterocyclic residue. Especially, groups represented by the formula

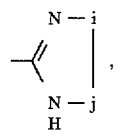

wherein i stands for —O— or —S—; j stands for >C=O, >C=S or >S(O)ₘ; and m is of the same meaning as defined above, (especially 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl) are preferable. The substitution position of R³ is, when the ring Y is phenyl for example, any one of ortho-, meta- and para- positions, and, among them, ortho-position is preferable.

And, while the above-mentioned heterocyclic residues (R³) include tautomers such as shown below, for example

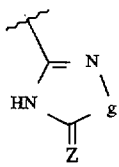

when Z=O, g=O,

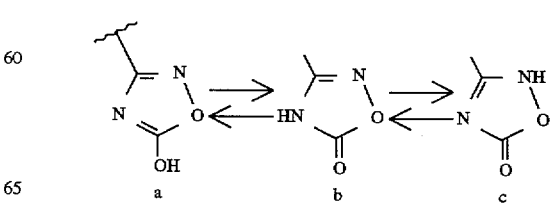

the heterocyclic residues represented by the formula

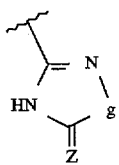

include all of the above-mentioned tautomers (a, b and c).

And, the above-mentioned heterocyclic residues ($R^3$) may optionally be substituted with a group represented by $R^{10}$, as shown below.

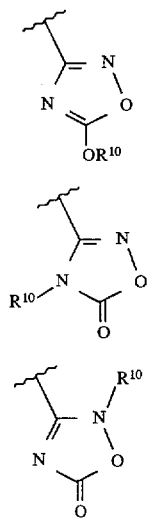

Examples of the group represented by $R^{10}$ include groups represented by the formula —CH($R^4$)—OCOR$^5$ [wherein $R^4$ stands for hydrogen, a $C_{1-6}$ straight-chain or branched lower alkyl group (e.g. methyl, ethyl, n-propyl, isopropyl, n-butyl, isobutyl, t-butyl, n-pentyl, isopentyl and neopentyl), a $C_{2-6}$ straight-chain or branched lower alkenyl group or a $C_{3-8}$ cycloalkyl group (e.g. cyclopentyl, cyclohexyl and cycloheptyl); and $R^5$ stands for a $C_{1-6}$ straight-chain or branched lower alkyl group (e.g. methyl, ethyl, n-propyl, isopropyl, n-butyl, isobutyl, sec-butyl, t-butyl, n-pentyl, isopentyl and neopentyl), a $C_{2-6}$ straight-chain or branched lower alkenyl group, a $C_{3-8}$ cycloalkyl group (e.g. cyclopentyl, cyclohexyl and cycloheptyl), a $C_{1-3}$ lower alkyl group substituted with a $C_{3-8}$ cycloalkyl group (e.g. cyclopentyl, cyclohexyl and cycloheptyl) or an optionally substituted aryl group such as phenyl (e.g. benzyl, p-chlorobenzyl, phenethyl, cyclopentylmethyl, cyclohexylmethyl), a $C_{2-3}$ lower alkenyl group optionally substituted with $C_{3-8}$ cycloalkyl or an optionally substituted aryl group such as phenyl (e.g. cinnamyl, etc. having alkenyl moiety such as vinyl, propenyl, allyl, and isopropenyl), an optionally substituted aryl group such as phenyl (e.g. phenyl, p-tolyl, naphthyl), a $C_{1-6}$ straight-chain or branched lower alkoxy group (e.g. methoxy, ethoxy, n-propoxy, isopropoxy, n-butoxy, isobutexy, sec-butexy, t-butoxy, n-pentyloxy, isopentyloxy and neopentyloxy), a $C_{2-8}$ straight, chain or branched lower alkenyloxy group (e.g. allyloxy and isobutenyloxy), a $C_{3-8}$ cycloalkyloxy group (e.g. cyclopentyloxy, cyclohexyloxy and cycloheptyloxy), a $C_{1-3}$ lower alkoxy group substituted with $C_{3-8}$ cycloalkyl (e.g. cyclopentyl, cyclohexyl and cycloheptyl) or an optionally substituted aryl group such as phenyl (e.g. benzyloxy, phenethyloxy, cyclopentylmethyloxy and cyclohexyl-methoxy having alkoxy moiety such as methoxy, ethoxy, n-propoxy and isopropoxy), a $C_{2-3}$ lower alkenyloxy group substituted with $C_{3-8}$ cycloalkyl (e.g. cyclopentyl, cyclohexyl and cycloheptyl) or an optionally substituted aryl group such as phenyl (e.g. cinnamyloxy having alkenyloxy moiety such as vinyloxy, propenyloxy, allyloxy, isopropenyloxy) and an optionally substituted aryloxy group such as phenoxy (e.g. phenoxy, p-nitrophenoxy and naphthoxy)], an optionally substituted alkyl (e.g. a lower ($C_{1-4}$) alkyl) or acyl (e.g. a lower ($C_{2-5}$) alkanoyl, an optionally substituted benzoyl). Examples of the substituent $R^{10}$ include methyl, ethyl, propyl, t-butyl, methoxymethyl, triphenylmethyl, cyanoethyl, acetyl, propionyl, pivaloyloxymethyl, 1-(cyclohexyloxycarbonyloxy)ethyl, (5-methyl-2-oxo-1,3-dioxolen-4-yl)methyl, acetoxymethyl, propionyloxymethyl, n-butyryloxymethyl, isobutyryloxymethyl, 1-(ethoxycarbonyloxy)ethyl, 1-(acetyloxy)ethyl, 1-(isobutyryloxy)ethyl, cyclohexylcarbonyloxymethyl, benzoyloxymethyl, cinnamyl and cyclopentylcarbonyloxymethyl, etc. As such groups as above, any one can be used, so long as they are such substituents (so-called prodrug) as being capable of readily converting, under biological or physiological conditions (e.g. in vivo reaction such as oxidation, reduction or hydrolysis catalyzed by in vivo enzymes), into a heterocyclic residue represented by the formula

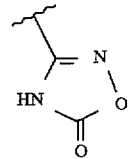

As tautomers of the above-mentioned heterocyclic residue (a, b and c) and the $R^{10}$-substituted heterocyclic residues (a', b' and c') are included in the heterocyclic residues as the substituent $R^3$, so the tautomers and their substituted structures of the above-mentioned various heterocyclic residues are likewise included in the substituent $R^3$ of the present invention. And, the substituent $R^3$ may have, besides the above-mentioned groups represented by $R^{10}$, further substituents, as exemplified by an optionally substituted alkyl group (e.g. methyl and triphenylmethyl, etc.), halogen (e.g. F, Cl and Br), nitro, cyano, a lower ($C_{1-4}$) alkoxy and an optionally substituted amino group (e.g. amino, methylamino and dimethylamino, etc.).

$R^3$ may also be a group such as a carboxyl, tetrazolyl, trifluoromethanesulfonamide (—NHSO$_2$CF$_3$), phosphoric acid, sulfonic acid, cyano or lower ($C_{1-4}$) alkoxycarbonyl group. These groups may be protected by a group such as an optionally substituted lower alkyl group, or an optionally substituted acyl group. Any group capable of forming an anion biologically or physiologically (e.g., biological reactions such as oxidation, reduction or hydrolysis caused by enzymes in the body) or chemically, or a group capable of changing thereto is acceptable.

$R^3$ is preferably a tetrazolyl or carboxyl group (preferably tetrazolyl group) which may be protected by an optionally substituted lower ($C_{1-4}$) alkyl group (e.g., methyl, triphenylmethyl, methoxymethyl, ethoxymethyl, p-methoxybenzyl, p-nitrobenzyl, etc.) or an optionally substituted acyl group (e.g., lower ($C_{2-5}$) alkanoyl, benzoyl, etc.). Although the position of $R^3$ may be ortho, meta or para, the ortho position is preferred.

X represents a bond between a adjacent phenylene group and phenyl group, whether direct or via a spacer having 2 or fewer atomic chains as the linear moiety (a direct bond is preferred). This spacer represents a divalent chain wherein the linear moiety consists of 1 or 2 atoms, and it may have a side chain. Such spacers include lower (C$_{1-4}$) alkylenes, —CO—, —O—, —S—, —NH—, —CO—NH—, —O—CH$_2$—, —S—CH$_2$— and —CH=CH—, etc. n represents the integer 1 or 2 (preferably 1).

The formula represented by the above-defined R$^3$, X and n:

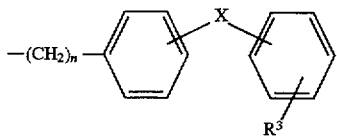

is preferably represented by the formula:

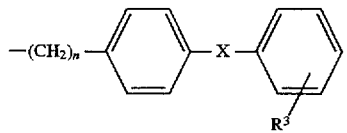

Typical examples of the nitrogen-containing heterocyclic ring residue for ring W are given below.

In the following formulas, R$^1$ is of the same meaning as defined above.

Example residues represented by formula (II):

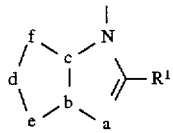
(II)

wherein a and e forming the heterocyclic residue are independently one or two optionally substituted carbon or hetero atoms; d and f forming the heterocyclic residue are independently one optionally substituted, carbon or hetero atom; b and c are independently one optionally substituted carbon or nitrogen atom, include the following:

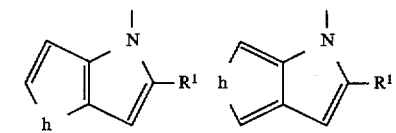

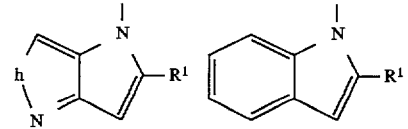

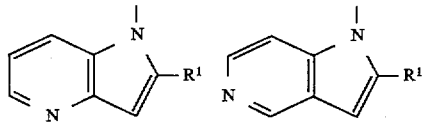

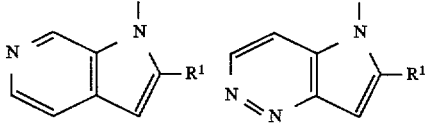

-continued

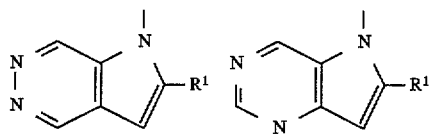

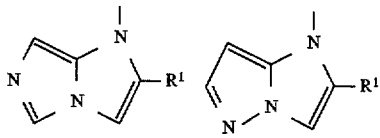

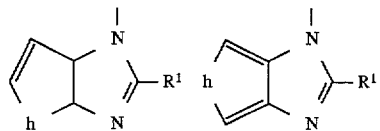

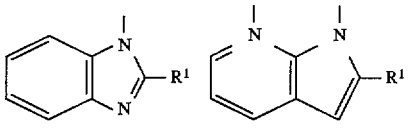

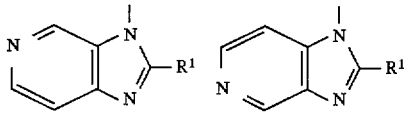

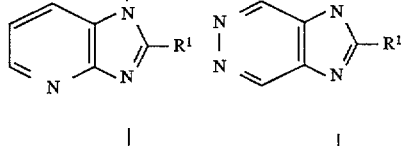

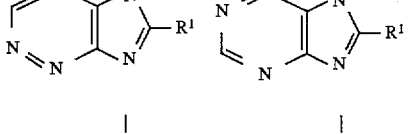

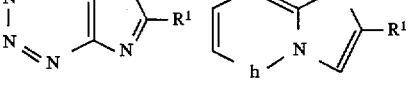

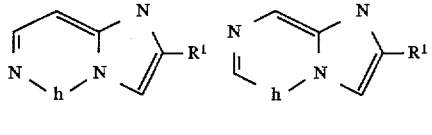

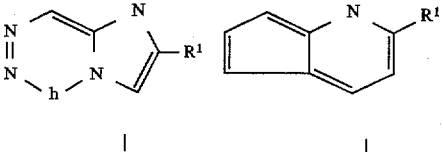

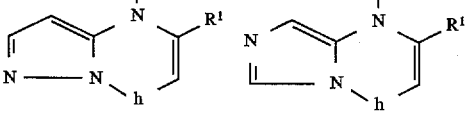

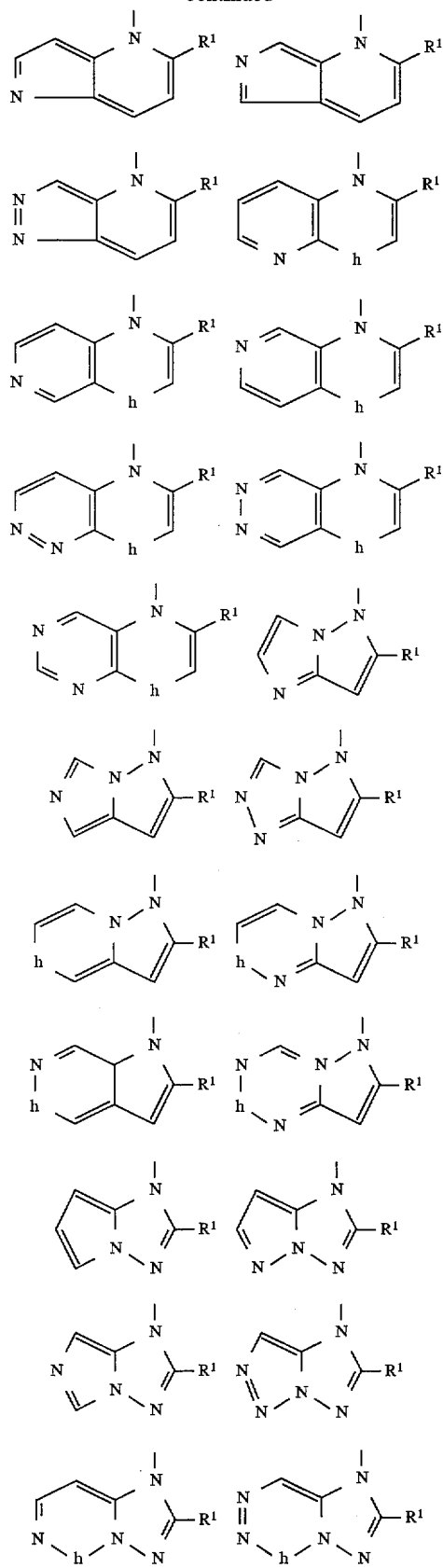

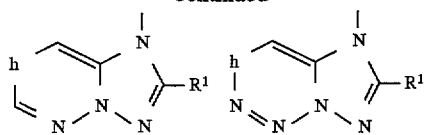

In the above formulas, h represents —CH$_2$—, >C=O, >C=S, >S—(O)$_m$, —N(R$^9$)— or —O—; m and R$^9$ are defined as above.

Example residues represented by formula (III):

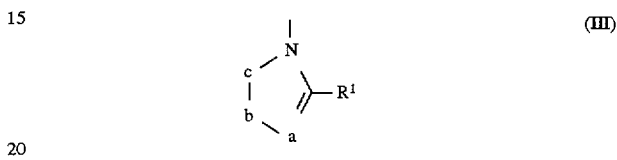

wherein a and b forming the heterocyclic residue are independently one or two optionally substituted carbon or hetero atoms; c is an optionally substituted carbon or hetero atom, include, but are not limited to, the following:

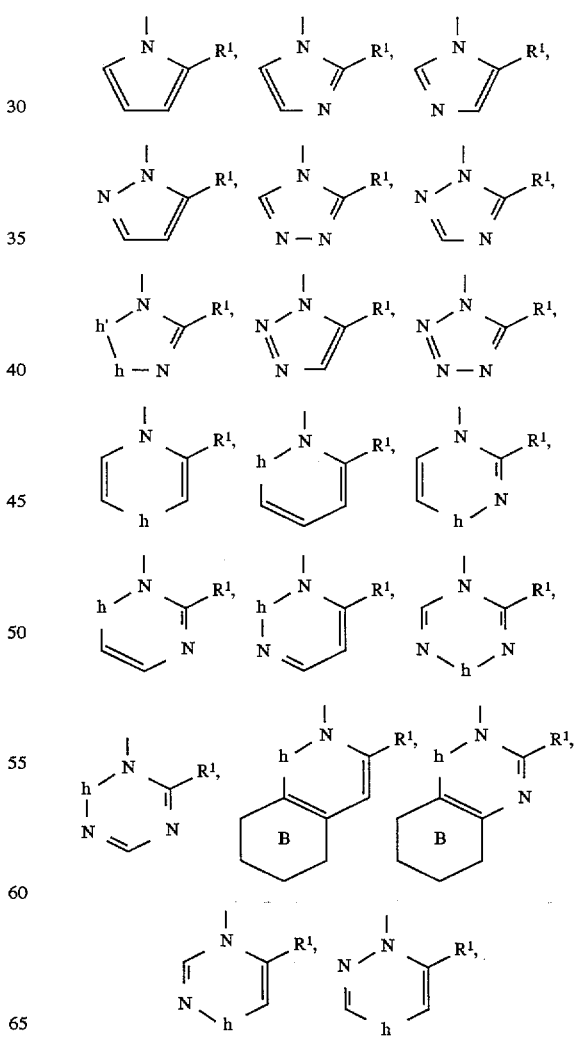

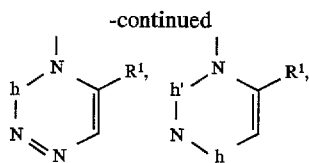

In the above formulas, B represents an aromatic hydrocarbon residue or heterocyclic residue (preferably an aromatic hydrocarbon residue such as benzene ring) which may be substituted and which may contain a hetero atom; h and h' independently represent —$CH_2$—, >C=O, >C=S, >S—$(O)_m$, —$N(R^9)$— or —O—; m and $R^9$ have the same definitions as above.

The heterocyclic ring residue represented by the above formula (II) may be substituted with a group represented by $R^2$ (e.g., a group capable of forming an anion or a group capable of changing thereto), besides a group represented by $R^1$. The substituent $R^2$ preferably binds on the atom fin formula (II).

The group capable of forming an union, or a group capable of changing thereto, for $R^2$, may be any one, as long as it is capable of forming an biologically or physiologically (e.g., biological reactions such as oxidation, reduction or hydrolysis caused by enzymes in the body) or chemically, or a group capable of changing thereto, and it may be protected by a group such as an optionally substituted lower alkyl group or an optionally substituted acyl group, and is exemplified by a carboxyl group which may be esterified or animated, tetrazolyl, trifluoromethanesulfonamide (—$NHSO_2CF_3$), phosphoric acid or sulfonic acid group, etc.

Examples of an optionally esterified or amidated carboxyl group represented by $R^2$ include groups represented by the formula —CO—D [wherein D stands for hydroxyl group, optionally substituted amino (e.g. amino, lower ($C_{1-4}$) alkylamino, and N,N-dilower ($C_{1-4}$) alkylamino, etc.) or optionally substituted alkoxy {e.g. a lower ($C_{1-6}$) alkoxy group, whose moiety is optionally substituted with hydroxyl group, optionally substituted amino (e.g. amino, dimethylamino, diethylamino, piperidino and morpholino, etc.), halogen, lower ($C_{1-6}$) alkoxy, lower ($C_{1-6}$) alkylthio or optionally substituted dioxolenyl (e.g. 5-methyl-2-oxo-1,3-dioxolen-4-yl, etc.), or a group represented by the formula —O—CH($R^4$)—O—$COR^5$ [wherein $R^4$ stands for hydrogen, a $C_{1-6}$ straight-chain or branched lower alkyl group (e.g. methyl, ethyl, n-propyl, isopropyl, n-butyl, isobutyl, t-butyl, n-pentyl, isopentyl and neopentyl), a $C_{2-6}$ straight-chain or branched lower alkenyl group or a $C_{3-8}$ cycloalkyl group (e.g. cyclopentyl, cyclohexyl and cycloheptyl), and $R^5$ stands for a $C_{1-6}$ straight-chain or branched lower alkyl group (e.g. methyl, ethyl, n-propyl, isopropyl, n-butyl, isobutyl, sec-butyl, t-butyl, n-pentyl, isopentyl and neopentyl), a $C_{2-6}$ straight-chain or branched lower alkenyl group, a $C_{3-8}$ cycloalkyl group (e.g. cyclopentyl, cyclohexyl and cycloheptyl), a $C_{1-3}$ lower alkyl group substituted with $C_{3-8}$ cycloalkyl (e.g. cyclopentyl, cylohexyl and cycloheptyl) or an optionally substituted aryl group such as phenyl (e.g. benzyl, p-chlorobenzyl, phenethyl, cyclopenty]methyl and cyclohexylmethyl), a $C_{2-3}$ lower alkenyl group optionally substituted with $C_{3-8}$ cycloalkyl or an optionally substituted aryl group such as phenyl (e.g. cinnamyl, etc. having alkenyl moiety such as vinyl, propenyl, allyl, and isopropenyl), an aryl group such as optionally substituted phenyl (e.g. phenyl, p-tolyl, naphthyl), a $C_{1-6}$ straight-chain or branched lower alkoxy group (e.g. methoxy, ethoxy, n-propoxy, isopropoxy, n-butoxy, isobutoxy, sec-butoxy, t-butoxy, n-pentyloxy, iso-pentyloxy and neopentyloxy), a $C_{2-8}$ straight-chain or branched lower alkenyloxy group (e.g. allyloxy and isobutenyloxy), a $C_{3-8}$ cycloalkyloxy group (e.g. cyclopentyloxy, cyclohexyloxy and cycloheptyloxy), a $C_{1-3}$ lower alkoxy group substituted with $C_{3-8}$ cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), a $C_{2-3}$ lower alkenyloxy group substituted with $C_{3-8}$ cycloalkyl (e.g. cyclopentyl, cyclohexyl and cycloheptyl) or an optionally substituted aryl group such as phenyl (e.g. cinnsmyloxy etc. having alkenyloxy moiety such as vinyloxy, propenyloxy, allyloxy, isopropenyloxy) and an optionally substituted aryloxy group such as phenoxy (e.g. phenoxy, p-nitrophenoxy and naphthoxy)}]. And, examples of the substituent represented by $R^2$ may also include a group capable of liberating proton or a group convertible thereinto in vivo (e.g. tetrazolyl, trifluoromethanesulfonic acid amide, phosphoric acid or sulfonic acid optionally protected with alkyl (e.g. a lower ($C_{1-4}$) alkyl), acyl (e.g. lower ($C_{2-5}$) alkanoyl or optionally substituted benzoyl, etc.). Examples of the substituent $R^2$ include —COOH and a salt thereof, —COOMe, —COOEt, —COOtBu, —COOPr, pivaloyloxymethoxycarbonyl, 1-(cyclohexyloxycarbonyloxy)ethoxycarbonyl, (5-methyl-2-oxo-1,3-dioxolen-4-yl)methoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl and cyclopentylcarbonyloxymethoxycarbonyl, etc. As such groups as above, mention is made of any one capable of liberating proton or a group convertible thereinto under biological or physiological conditions (e.g. in vivo reaction such as oxidation, reduction or hydrolysis catalyzed by in vivo enzymes). $R^2$ may be a carboxyl group or a prodrug thereof. $R^2$ may also be groups convertible into anion in vivo, biologically or chemically.

And, a compound, in which $R^2$ is a group capable of liberating proton or a group chemically (e.g. oxidation, reduction or hydrolysis, etc.) convertible thereinto (e.g. optionally protected carboxyl group, tetrazolyl group, carbaldehyde group and hydroxymethyl group; and cyano group), is useful as synthetic intermediate.

Among the groups described as $R^2$, preferable ones include carboxyl, esterified carboxyl (e.g. methyl ester, ethyl ester or an ester formed by binding of a group represented by the above-mentioned formula —O—CH($R^4$)— $OCOR^5$ to carbonyl) and optionally protected tetrazolyl, carboaldehyde and hydroxymethyl.

The heterocyclic residue represented by formula (II) may optionally have, besides the groups represented by $R^1$ and $R^2$, further substitutents represented by Q, as exemplified by halogen (e.g., F, Cl, Br), cyano, nitro, lower ($C_{1-4}$) alkyl, lower ($C_{1-4}$) alkoxy, amino groups which may be substituted (e.g., amino, N-lower ($C_{1-4}$) alkylamino (e.g., methylamino, etc.), N,N-dilower ($C_{1-4}$) alkylamino (e.g., dimethylamino, etc.), N-arylamino (e.g., phenylamino, etc.), allcyclic amino (e.g., morpholino, piperidino, piperazino, N-phenylpiperazino, etc.)), groups represented by the formula —CO—D' [D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyioxy, etc.), or lower ($C_{1-6}$)

alkoxycarbonyloxy (e.g., methoxycarbonyloxy, ethoxycarbonyloxy, cyclohexyloxycarbonyloxy, etc.)], and tetrazolyl, trifluoromethanesulfonamide, phosphoric acid and sulfonic acid groups which may be protected by a lower ($C_{1-4}$) alkyl or acyl (e.g., lower ($C_{2-5}$) alkanoyl, benzoyl which may be substituted), with preference given to lower ($C_{1-4}$) alkyl and halogen. One or two of these substituents may be concurrently present at any positions on the ring.

Preferable condensed heterocyclic rings represented by formula (II) include the following:

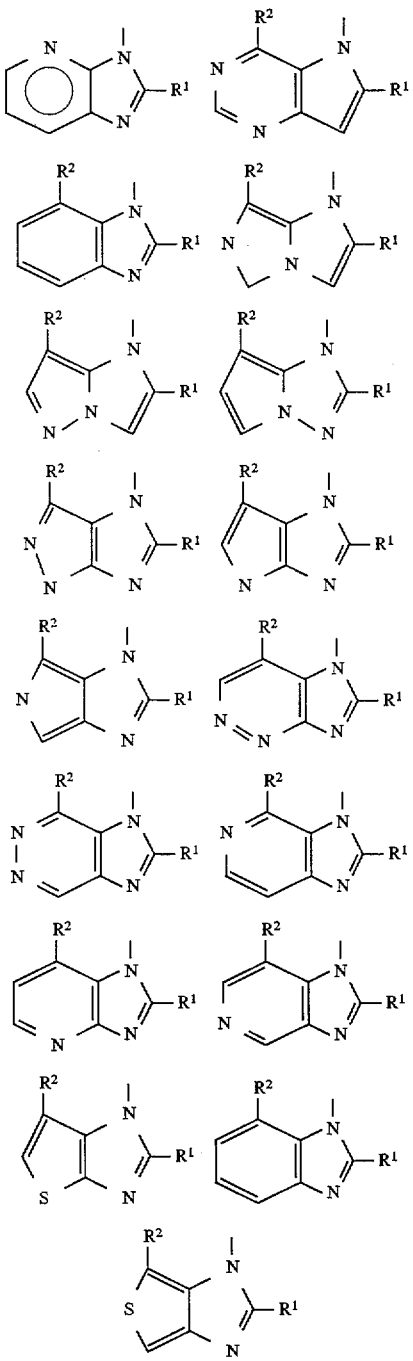

wherein $R^1$ and $R^2$ have the same definitions as above. Specifically, compounds having a benzimidazole, thienoimidazole or imidazopyridine (preferably benzimdazole or thienoimidazole) skeleton are preferred.

The heterocyclic residue represented by the formula (III) may optionally have, besides the group represented by $R^1$, further substituents. Such substituents include halogen (e.g., F, Cl, Br), cyano, nitro, an optionally substituted lower ($C_{1-4}$) alkyl, an optionally substituted lower ($C_{1-4}$) allyloxy, an optionally substituted amino group (e.g., amino, N-lower ($C_{1-4}$) alkylamino (e.g., methylamino, etc.), N,N-dilower ($C_{1-4}$) alkylamino (e.g., dimethylamino, etc.), N-arylamino (e.g., phenylamino, etc.), allcyclic amino (e.g., morpholino, piperidino, piperamino, N-phenylpiperazino, etc.)), groups represented by the formula —CO—D'[D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyloxy, etc.) or lower ($C_{1-6}$) alkoxycarbonyloxy (e.g., methoxycarbonyloxy, ethoxycarbonyloxy, cyclohexyloxycarbonyloxy, etc.)], and tetrazolyl, trifluoromethanesulfonamide, phosphoric acid and sulfonic acid groups which may be protected by a lower ($C_{1-4}$) alkyl or acyl (e.g., lower ($C_{2-5}$) alkanoyl, benzoyl which may be substituted), with preference given to an optionally substituted lower ($C_{1-4}$) alkyl and halogen. One or two of these substituents may be concurrently present at any positions on the ring. Substituents on the optionally substituted lower ($C_{1-4}$) alkyl group include a hydroxyl group, a carboxyl group and halogen.

The above-described salt is exemplified by pharmacologically acceptable salts such as those with inorganic bases, those with organic bases, those with inorganic acids, those with organic acids and those with basic or acidic amino acids. Preferable salts with inorganic bases include alkali metal salts such as sodium salt and potassium salt, alkaline earth metal salts such as calcium salt and magnesium salt, aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine, etc. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic add, benzenesulfonic acid and p-toluenesulfonic acid. Preferable salts with basic amino acids include salts with arginine, lysine and omitkine. Preferable salts with acidic areno acids include salts with aspartic acid and glutstoic acid.

Of the compounds represented by the above formula (I), preference is given to compounds (or salts thereof) represented by the formula (I'):

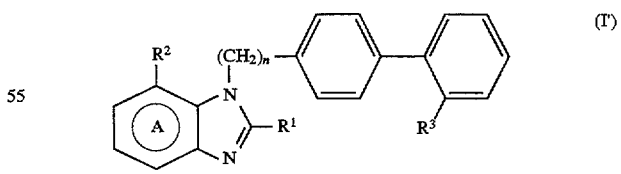

wherein ring A is a benzene ring which may have a substituent in addition to the group $R^2$; $R^1$ represents hydrogen or an optionally substituted lower ($C_{1-6}$) alkyl (preferably a lower ($C_{1-4}$) alkyl) which binds through a hetero atom (e.g. O, N(H) and S); $R^2$ is a group represented by the formula —CO—D'' [wherein D'' stands for hydroxyl group, amino, N-lower ($C_{1-4}$) alkylamino, N,N-dilower ($C_{1-4}$) alkylamino or a lower ($C_{1-4}$) alkoxy whose alkyl moiety is optionally substituted with hydroxyl group, amino, halogen, a lower ($C_{2-6}$) alkanoyloxy (e.g. acetyloxy and pivaloyloxy, etc.), lower ($C_{4-7}$) cycloalkanoyloxy, lower ($C_{1-6}$) alkoxycarbonyloxy (e.g. methoxycarbonyloxy, ethoxycarbonyloxy), lower ($C_{3-7}$) cycloalkoxycarbonyloxy (e.g. cyclohexyloxycarbonyloxy) or a lower ($C_{1-4}$) alkoxy; $R^3$ stands for a tetrazolyl, carboxyl group or groups represented by the formula

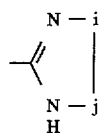

wherein i stands for —O— or —S—; j stands for >C=O, >C=S or >S(O)$_m$; and m is of the same meaning as defined above, which are optionally protected with optionally substituted lower ($C_{1-4}$) alkyl (e.g. methyl, triphenylmethyl, methoxymethyl, acetyloxymethyl, methoxycarbonyloxymethyl, ethoxycarbonyloxymethyl, 1-(cyclohexyloxycarbonyloxy)ethyl and pivaloyloxymethyl, etc.) or an acyl group (e.g. a lower ($C_{2-5}$ alkanoyl and benzoyl, etc.).

In the formula (I'), substituents on the optionally substituted lower alkyl for $R^1$ include a hydroxy group, an amino group, halogen and a lower ($C_{1-4}$) alkoxy group.

In the formula (I'), ring A is a benzene ring which may have a substituent, in addition to the group $R^2$, such as a halogen (e.g., F, Cl, Br), lower ($C_{1-4}$) alkyl, lower ($C_{1-4}$) alkoxy, nitro, a group represented by the formula —CO—D'|D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyloxy, etc.) or lower ($C_{1-6}$) alkoxycarbonyloxy (e.g., methoxycarbonyloxy, ethoxycarbonyloxy, cyclohexyloxycarbonyloxy)], or an amino which may be substituted with a lower ($C_{1-4}$) alkyl (preferably a substituent such as a lower $C_{1-4}$) alkyl or halogen) (more preferably a benzene ring which has no substituent in addition to the group represented by the formula $R^2$).

Preferable compounds for use as an active ingredient of the present invention are exemplified by those mentioned in Examples of Japanese Patent Unexamined Publication Nos. 364171/1992 and EP 520423.

Compounds represented by formula (I) are disclosed in Japanese Patent Unexamined Publication Nos. 9373/1992 and 364171/1992, EP 520423 and other publications, and can be produced according to the disclosure.

The angiotensin II antagonizing compounds (or salts thereof of the present invention, represented by general formula (I), can be used as a pharmaceutical at low toxicity in animals, particularly mammals (e.g., humans, dogs, rabbits, rats, mice) to suppress vascular hypertrophy, specifically to suppress and prevent or treat vascular hypertrophy (including restenosis) after percutaneous transluminal coronary angioplasty (PTCA), vascular restenosis after bypass surgery and progress of arteriosclerosis. The compounds (or salts thereof represented by general formula (I) can be orally or non-orally used by inhalation, rectal injection or local administration. It can be used as a pharmaceutical composition or preparation (e.g., powders, granules, tablets, pills, capsules, injectable preparations, syrups, emulsions, elixirs, suspensions, solutions), which may contain one or more inventive compounds with pharmaceutically acceptable carriers (e.g., adjuvants, excipients, shaping agents and/or diluents).

Pharmaceutical compositions can be prepared as pharmaceutical preparations by ordinary methods. In the present specification, "non-oral" includes subcutaneous injection, intravenous injection, intramuscular injection, intraperitoneal injection and drip infusion. Injectable preparations, e.g., aqueous or oily suspensions for aseptic injection, can be prepared by methods known in relevant fields, using an appropriate dispersing agent or wetting agent and a suspending agent. The aseptic injectable preparation thus obtained may be an aseptically injectable solution or suspension in a diluent or solvent which permits non-toxic non-oral administration, such as an aqueous solution. Acceptable vehicles or solvents include water, Ringer's solution and isotonic saline. It is also possible to use aseptic non-volatile oils in common use as solvents or suspending media.

For this purpose any non-volatile oil or fatty acid can be used, including natural, synthetic or semi-synthetic fatty oils or acids, and natural, synthetic or semi-synthetic mono- or di- or tri-glycerides.

Suppositories for rectal administration may be produced as a mixture of the drug and an appropriate non-irritative shaping agent which is solid at normal temperatures and which is liquid at intestinal temperatures and melts and releases the drug in the rectum, such as cacao butter or polyethylene glycol.

Solid dosage forms for oral administration include the above-mentioned ones such as powders, granules, tablets, pills and capsules. In these dosage forms, the active ingredient compound may be mixed with at least one additive such as sucrose, lactose, cellulose sugar, mannitol, maltitol, dextran, starch, agar, alginate, chitin, chitosan, pectin, gum tragacanth, arabic, gelatin, collagen, casein, albumin, synthetic or semi-synthetic polymer or glyceride. Such dosage forms may contain additional additives as usual, including inert diluents, lubricants such as magnesium stearate, preservatives such as paraben and sorbic acid, antioxidants such as aseorbic acid, α-tocopherol and cysteine, disintegrating agents, binders, hypertrophy agents, buffers, sweeteners, flavoring agents and perfumes. Tablets and pills may be produced with enteric coating. Liquid dosage forms for oral administration include pharmaceutically acceptable emulsions, syrups, elixirs, suspensions and solutions, which may contain inert diluents, such as water, in common use in relevant fields.

The dose for a particular patient is determined according to age, body weight, general health status, sex, dietary status, administration time, method of administration, excretion rate, drug combination, the severity of the illness being treated and other factors.

The compounds (or salts thereof represented by general formula (I) can be safely used at low toxicity. Its daily dose, varying depending on the patient's condition, body weight, type of compound, route of administration and other factors, is normally about 0.01 to 50 mg/kg/day, preferably 0.01 to 20 mg/kg/day for non-oral routes such as subcutaneous, intravenous, intramuscular and rectal administration, and about 0.01 to 150 mg/kg/day, preferably 0.1 to 100 mg/kg/day for oral administration. Bioactivity of an angiotensin II antagonistic compounds (or salts thereof) are described by means of the following test example.

Test Example 1

Suppressing Action Against Vascular Hypertrophy Due to Endothelial Damage in Rats Compound 1: (±)-1-(cyclohexyloxycarbonyloxy) ethyl 2-ethoxy-1-[[2'-(1H-tetrazol-5-yl)biphenyl-4-yl]methyl]benzimidazole-7-carboxylate Male SD rats, at 9 to 12 weeks old, were used. Under pentobarbital anesthesia (50 mg/kg, j.p.), each animal's left femoral and common carotid arteries were exposed, and a balloon catheter (Fogmy 12-060-2F, Baxter) was passed from the left femoral artery to the left common carotid artery. The catheter was further passed to the internal and external carotid bifurcation; and the balloon was then inflated by air injection and pulled about 1.5 cm in the tail direction to injure the vascular endotheHum. After balloon catheter removal, an antibiotic (synthetic penicillin) was dripped, and the wounds were sutured.

After suspension in gum arabic, each drug was orally administered in a volume of 2 ml/kg once daily from 6 days before endothelial injury. A 5% grams arabic solution was administered to the control group.

Intimal and medial tunica hypertrophy was quantified as follows: Under pentobarbital anesthesia (50 mg/kg, j.p.), rats were given 2% Evans blue (dissolved in heparin-containing physiological saline) at 250 µl/rat via the tail vein. About 20 minutes later, each animal was laparotomized, and the abdominal vena cava incised to cause bleeding. At the same time the animal was thoracotomized, and a polyethylene tube was passed from the left ventricle and physiological saline was circulated, after which 10% neutral buffered formalin solution (pH 7.2) was perfused for fixation in situ. The left common carotid artery was excised, and the portion stained blue with Evans blue was taken as a specimen. After fixation with the same fixative, the specimen was equally divided into two segment and each embedded in paraffin. Two cross-sections per segment (each 500 µm apart) were cut. Four thin sections of each animal were stained with hematoxylin-eosine and examined using a microscopic image analyzer (IBAS 2000, Zeiss) to determine intimal and medical tunica areas.

As seen in Table 1, marked hypertrophy was observed in the control group 14 days after endothelial injury. When compound 1 was orally administered at 1 mg/kg/day and 10 mg/kg/day from 6 days before endothelial injury, this intimal hypertrophy was suppressed by 43% and 58%, respectively ($p<0.01$). Cilazapril, an angiotensin-converting enzyme inhibitor, at 10 mg/kg/day, showed a suppression of 48% ($p<0.05\%$). With respect to medical tunica hypertrophy, cilazapril (10 mg/kg/day) showed no significant effect, while compound 1 showed a significant ($p<0.01$) suppressing effect at a low dose of 1 mg/kg/day.

These results demonstrate that compound 1 suppresses, vascular hypertrophy after endothelial injury, suggesting that compound 1 is effective in preventing restenosis after percutaneous transluminal coronary angioplasty (PTCA) and progression of arteriosclerosis.

TABLE 1

Suppressive Action Against Vascular Hypertrophy Following Rat Carotic Arterial Endothelial Injury

| Group | Dose (mg/kg/day) | Initimal Tunica Area (mm$^2$) | | Medial Tunica Area (mm$^2$) | |
|---|---|---|---|---|---|
| Experiment 1 | | | | | |
| Control group | — | 0.130 ± 0.026 | (8) | 0.114 ± 0.008 | (6) |
| Compound 1 | 1 | 0.074 ± 0.041++ | (7) | 0.094 ± 0.011++ | (7) |
| Experiment 2 | | | | | |
| Control group | — | 0.172 ± 0.056 | (7) | 0.120 ± 0.012 | (7) |
| Compound 1 | 10 | 0.073 ± 0.036++ | (7) | 0.095 ± 0.007++ | (7) |
| Cilazapril | 10 | 0.089 ± 0.036+ | (6) | 0.107 ± 0.011 | (6) |

Significance level against control group: +: $p<0.05$; ++: $p<0.01$ Figures in parentheses show the number of subject rats.

[EXAMPLES]

The present invention is hereinafter described in more detail by means of the following examples, but the scope of the invention is not limited to the examples.

Examples

Preparation Examples

A vascular hypertrophy suppressor containing inventive compound (I) (or salt thereof) as an active ingredient can, for example, be produced with the following formulations:

1. Capsules

| | | |
|---|---|---|
| (1) | 2-ethoxy-1-[[2'-(1H-tetrazol-5-yl)biphenyl-4-yl]-methyl]-1H-benzimidazole-7-carboxylic acid | 10 mg |
| (2) | Lactose | 90 mg |
| (3) | Microcrystalline cellulose | 70 mg |
| (4) | Magnesium stearate | 10 mg |
| | Total | 180 mg per capsule |

Components (1), (2), (3) and a half portion of component (4) were mixed and granulated. To these granules, the remaining portion of component (4) Was added, and the whole mixture packed in a gelatin capsule.

2. Tablets

| | | |
|---|---|---|
| (1) | 2-ethoxy-1-[[2'-(1H-tetrazol-5-yl)biphenyl-4-yl]-methyl]-1H-benzimidazole-7-carboxylic acid | 10 mg |
| (2) | Lactose | 35 mg |
| (3) | Corn starch | 150 mg |
| (4) | Microcrystalline cellulose | 30 mg |
| (5) | Magnesium stearate | 5 mg |
| | Total | 230 mg per tablet |

Components (1), (2), (3), a two-thirds portion of component (4) and a half portion of component (5) were mixed and granulated. To these granules, the remaining portions of components (4) and (5) added, and the whole mixture tableted by compressive tableting.

3. Injectable preparations

| | | |
|---|---|---|
| (1) | 2-methylthio-1-[[2'-(1H-tetrazol-5-yl)-biphenyl-4-yl]methyl]-1H-benzimidazole-7-carboxylic acid disodium salt | 10 mg |
| (2) | Inositol | 100 mg |
| (3) | Benzyl alcohol | 20 mg |
| | Total | 130 mg per ampule |

Components (1), (2) and (3) were dissolved in distilled water for injection to a final quantity of 2 ml, and the solution was packed in an ampule. The entire procedure was performed aseptically.

4. Capsules

| | | |
|---|---|---|
| (1) | (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 10 mg |

| 4. Capsules | | |
|---|---|---|
| (2) Lactose | 90 mg | |
| (3) Microcrystalline cellulose | 70 mg | |
| (4) Magnesium stearate | 10 mg | |
| | Total | 180 mg per capsule |

Components (1), (2), (3) and a half portion of component (4) were mixed and granulated. To these granules, the remaining portion of component (4) was added, and the whole mixture packed in a gelatin capsule.

| 5. Tablets | | |
|---|---|---|
| (1) (±)-1-(cyclohexyloxycarbonyloxy)ethyl 2-ethoxy-1-[[2'-(1H-tetrazol-5-yl)biphenyl-4-yl]methyl]-1H-benzimidazole-7-carboxylate | 10 mg | |
| (2) Lactose | 35 mg | |
| (3) Corn starch | 150 mg | |
| (4) Microcrystalline cellulose | 30 mg | |
| (5) Magnesium stearate | 5 mg | |
| | Total | 230 mg per tablet |

Components (1), (2), (3), a two-thirds portion of component (4) and a half portion of component (5) were mixed and granulated. To these granules, the remaining portions of components (4) and (5) were added, and the whole mixture tableted by compressive tableting.

| 6. Injectable preparations | | |
|---|---|---|
| (1) 2-ethoxy-1-[[2'-(1H-tetrazol-5-yl)biphenyl-4-yl]methyl]-1H-benzimidazole-7-carboxylic acid disodium salt | 10 mg | |
| (2) Inositol | 100 mg | |
| (3) Benzyl alcohol | 20 mg | |
| | Total | 130 mg per ampule |

Components (1), (2) and (3) were dissolved in distilled water for injection to a final quantity of 2 ml, and the solution was packed in an ampule. The entire procedure was performed aseptically.

| 7. Capsules | | |
|---|---|---|
| (1) 2-ethoxy-1-[[2'-(4,5-dihydro-5-oxo-1,2,4-oxadiazol-3-yl)biphenyl-4-yl]methyl]-1H-benzimidazole-7-carboxylic acid | 10 mg | |
| (2) Lactose | 90 mg | |
| (3) Microcrystalline cellulose | 70 mg | |
| (4) Magnesium stearate | 10 mg | |
| | Total | 180 mg per capsule |

Components (1), (2), (3) and a half portion of component (4) were mixed and granulated. To these granules, the remaining portion of component (4) was added, and the whole mixture packed in a gelatin capsule.

| 8. Tablets | | |
|---|---|---|
| (1) 2-ethoxy-1-[[2'-(4,5-dihydro-5-oxo-1,2,4-oxadiazol-3-yl)biphenyl-4-yl]methyl]-1H-benzimidazole-7-carboxylic acid i- | 10 mg | |
| (2) Lactose | 35 mg | |
| (3) Corn starch | 150 mg | |
| (4) Microcrystalline cellulose | 30 mg | |
| (5) Magnesium stearate | 5 mg | |
| | Total | 230 mg per tablet |

Components (1), (2), (3), a two-thirds portion of component (4) and a half portion of component (5) were mixed and granulated. To these granules, the remaining portions of components (4) and (5) were added, and the whole mixture tableted by compressive tableting.

| 9. Capsules | | |
|---|---|---|
| (1) Pivaloyloxymethyl 2-ethoxy-1-[[2'-(1H-tetrazol-5-yl)biphenyl-4-yl]methyl]-1H-benzimidazole-7-carboxylate | 10 mg | |
| (2) Lactose | 90 mg | |
| (3) Microcrystalline cellulose | 70 mg | |
| (4) Magnesium stearate | 10 mg | |
| | Total | 180 mg per capsule |

Components (1), (2), (3) and a half portion of component (4) were mixed and granulated. To these granules, the remaining portion of component (4) was added, and the whole mixture packed in a gelatin capsule.

| 10. Tablets | | |
|---|---|---|
| (1) Pivaloyloxymethyl 2-ethoxy-1-[[2'-(1H-tetrazol-5-yl)biphenyl-4-yl]methyl]-1H-benzimidazole-7-carboxylate | 10 mg | |
| (2) Lactose | 35 mg | |
| (3) Corn starch | 150 mg | |
| (4) Microcrystalline cellulose | 30 mg | |
| (5) Magnesium stearate | 5 mg | |
| | Total | 230 mg per tablet |

Components (1), (2), (3), a two-thirds portion of component (4) and a half portion of component (5) were mixed and granulated. To these granules, the remaining portions of components (4) and (5) were added, and the whole mixture tableted by compressive tableting.

What is claimed is:

1. A method for the prophylaxis or treatment of vascular hypertrophy in a mammal by administering thereto a pharmaceutically effective amount of a compound of the following formula (I), or a salt thereof:

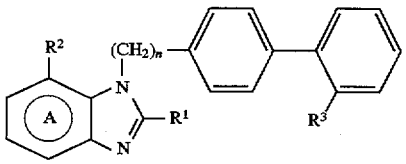

wherein:

A is a substituted or unsubstituted benzene ring having the substituent $R^2$;

$R^1$ is alkyl, alkenyl, alkynyl or cycloalkyl which binds through a group of the formula: —N($R^9$)— wherein $R^9$ is hydrogen or lower ($C_{1-4}$) alkyl, —O— or —S(O)$_m$— wherein m is an integer of 0 to 2 and which may be substituted with hydroxy, optionally substituted amino, halogen, lower ($C_{1-4}$) alkoxy or lower ($C_{1-4}$) alkylthio; or $R^1$ is aryl or aralkyl which may bind through a group of the formula: —N($R^9$)— wherein $R^9$ is hydrogen or lower ($C_{1-4}$) alkyl, —O— or —S(O)$_m$— wherein m is an integer of 0 to 2 and which may be substituted with halogen, nitro, optionally substituted amino, lower ($C_{1-4}$) alkoxy, lower ($C_{1-4}$) alkylthio or lower ($C_{1-4}$) alkyl;

$R^2$ is optionally esterified or amidated carboxyl, tetrazolyl, trifluoromethanesulfonic amide, phosphoric acid or sulfonic acid, which may be protected with optionally substituted lower alkyl or acyl;

$R^3$ is one of the following:

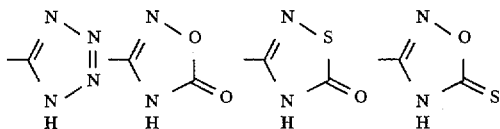

and n is 1 or 2.

2. The method of claim 1 wherein $R^1$ is lower ($C_{1-8}$) alkyl, lower ($C_{2-8}$) alkenyl or lower ($C_{3-6}$) cycloalkyl which binds through a group of the formula: —N($R^9$)— wherein $R^9$ is hydrogen or lower ($C_{1-4}$) alkyl, —O— or —S(O)$_m$— wherein m is an integer of 0 to 2 and which may be substituted with hydroxy, amino, N-lower ($C_{1-4}$) alkylamino, N,N-dilower ($C_{1-4}$) alkylamino, halogen, lower ($C_{1-4}$) alkoxy or lower ($C_{1-4}$) alkylthio.

3. The method of claim 1 wherein $R^1$ is alkyl or alkenyl which binds through a group of the formula: —N($R^9$)— wherein $R^9$ is hydrogen or lower ($C_{1-4}$) alkyl, —O— or —S(O)$_m$— wherein m is an integer of 0 to 2 and which may be substituted with hydroxy, optionally substituted amino, halogen, lower ($C_{1-4}$) alkoxy or lower ($C_{1-4}$) alkylthio.

4. The method of claim 1 wherein $R^2$ is a group of the formula: —CO—D wherein D is hydroxy, optionally substituted amino or optionally substituted alkoxy.

5. The method of claim 4 wherein the optionally substituted alkoxy is lower ($C_{1-6}$) alkoxy whose alkyl moiety may be substituted with hydroxy, optionally substituted amino, halogen, lower ($C_{1-6}$) alkoxy, lower ($C_{1-6}$) alkylthio or optionally substituted dioxolenyl, or a group of the formula: —O—CH($R^4$)—OCOR$^5$ wherein $R^4$ is hydrogen, lower ($C_{1-6}$) alkyl, lower ($C_{2-6}$) alkenyl or lower ($C_{3-8}$) cycloalkyl; and $R^5$ is lower ($C_{1-6}$) alkyl, lower ($C_{2-6}$) alkenyl, lower ($C_{3-8}$) cycloalkyl, lower ($C_{1-3}$) alkyl substituted with lower ($C_{3-8}$) cycloalkyl or aryl, lower ($C_{2-3}$) alkenyl optionally substituted with lower ($C_{3-8}$) cycloalkyl or aryl, aryl, lower ($C_{1-6}$) alkoxy, lower ($C_{2-8}$) alkenyloxy, lower ($C_{3-8}$) cycloalkyloxy, lower ($C_{1-3}$) alkoxy substituted with lower ($C_{3-8}$) cycloalkyl or aryl, lower ($C_{2-3}$) alkenyloxy substituted with lower ($C_{3-8}$) cycloalkyl or aryl, or aryloxy.

6. The method of claim 1 wherein $R^2$ is optionally esterified carboxy.

7. The method of claim 1 wherein n is 1.

8. The method of claim 1 wherein said compound of formula (I) is 2-ethoxy-1-[[2'-(1H-tetrazol-5-yl)biphenyl-4-yl]methyl]-1H-benzimidazole-7-carboxylic acid.

9. The method of claim 1 wherein said compound of formula (I) is pivaloyloxymethyl 2-ethoxy-1-[[2'-(1H-tetrazol-5-yl)biphenyl-4-yl]methyl]-1H-benzimidazole-7-carboxylate.

10. The method of claim 1 wherein said compound of formula (I) is 2-ethoxy-1-[[2'-(4,5-dihydro-5-oxo-1,2,4-oxadiazol-3-yl)biphenyl-4-yl]methyl]-1H-benzimidazole-7-carboxylic.

11. The method of claim 1 wherein said vascular hypertrophy occurs after percutaneous transluminal coronary angioplasty.

12. The method of claim 1 wherein said vascular hypertrophy occurs after bypass surgery.

13. The method of claim 1 wherein said vascular hypertrophy occurs due to arteriosclerosis.

14. The method of claim 1 wherein the method is a method of treatment of vascular hypertrophy.

15. The method of claim 8 wherein the method is method of treatment of vascular hypertrophy.

16. The method of claim 10 wherein the method is a method of treatment of vascular hypertrophy.

17. The method of claim 4 wherein the method is a method of treatment of vascular hypertrophy.

18. The method of claim 11 wherein said compound is 2-ethoxy-1-[[2'-(1H-tetrazol-5-yl)biphenyl-4-yl]methyl]-1H-benzimidazole-7-carboxylic acid or a pharmaceutically acceptable salt thereof.

19. The method of claim 1 wherein said compound 2-ethoxy-1-[[2'-(4,5-dihydro-5-oxo-1,2,4-oxadiazol-3-yl)biphenyl-4-yl]methyl]-1H-benzimidazole-7-carboxylic acid or a pharmaceutically acceptable salt thereof.

20. The method of claim 12 wherein said compound is 2-ethoxy-1-[[2'-(1H-tetrazol-5-yl)biphenyl-4-yl ]methyl]-1H-benzimidazole-7-carboxylic acid or a pharmaceutically acceptable salt thereof.

21. The method of claim 12 wherein said compound is 2-ethoxy-1-[[2'(4,5-dihydro-5-oxo-1,2,4-oxadiazol-3-yl)biphenyl-4-yl]methyl]-1H-benzimidazole-7-carboxylic acid or a pharmaceutically acceptable salt thereof.

* * * * *

UNITED STATES PATENT AND TRADEMARK OFFICE
CERTIFICATE OF CORRECTION

PATENT NO. :   5,736,561
DATED      :   April 7, 1998
INVENTOR(S):   Kohei NISHIKAWA It is certified that error appears in the above-identified patent and that said Letters Patent is hereby corrected as shown below:

Column 23, line 1, delete "-S()$_m$-" and insert -- -S(O)$_m$- --. Column 23, line 6, delete "may bind" and insert --binds--. Column 24, line 39, delete "claim 1" and insert --claim 11--. Column 24, line 48, delete "[[2'(4,5-" and insert -- "[[2'-(4,5- --.

Signed and Sealed this

Twelfth Day of January, 1999

Attest:

Attesting Officer

Acting Commissioner of Patents and Trademarks